United States Patent
Steiner et al.

(10) Patent No.: US 6,991,779 B2
(45) Date of Patent: Jan. 31, 2006

(54) COMPOSITIONS FOR TREATMENT OR PREVENTION OF BIOTERRORISM

(75) Inventors: Solomon S. Steiner, Mount Kisco, NY (US); Cohava Gelber, Hartsdale, NY (US); Robert S. Feldstein, Yonkers, NY (US); Roderike Pohl, Sherman, CT (US)

(73) Assignee: MannKind Corporation, Valencia, CA (US)

( * ) Notice: Subject to any disclaimer, the term of this patent is extended or adjusted under 35 U.S.C. 154(b) by 238 days.

(21) Appl. No.: 10/347,932

(22) Filed: Jan. 17, 2003

(65) Prior Publication Data

US 2004/0018152 A1 Jan. 29, 2004

Related U.S. Application Data

(60) Provisional application No. 60/349,628, filed on Jan. 18, 2002.

(51) Int. Cl.
*A61K 9/12* (2006.01)
*A61K 9/72* (2006.01)

(52) U.S. Cl. .................. 424/45; 424/493; 424/489; 424/490; 128/200.14

(58) Field of Classification Search .................. 424/45, 424/493, 489, 490, 46, 434; 128/200.14; 514/249
See application file for complete search history.

(56) References Cited

U.S. PATENT DOCUMENTS

| 5,352,461 | A | 10/1994 | Feldstein et al. | |
|---|---|---|---|---|
| 5,503,852 | A | 4/1996 | Steiner et al. | |
| 6,071,497 | A | 6/2000 | Steiner et al. | |
| 6,253,762 | B1 * | 7/2001 | Britto | 128/200.14 |
| 2002/0187984 | A1 * | 12/2002 | Boyce et al. | 514/249 |

OTHER PUBLICATIONS

Drug Information Handbook, (Lacy et al) 1993, pp. 81-82, Lexi-Comp,Inc.*

* cited by examiner

*Primary Examiner*—Sreeni Padmanabhan
*Assistant Examiner*—Mina Haghighatian
(74) *Attorney, Agent, or Firm*—Pabst Patent Group LLP

(57) ABSTRACT

Compositions containing biologically active molecules encapsulated in self-assembling, diketopiperazine microspheres (TECHNOSPHEREs™) and methods for making and administering such compositions are described herein. The compositions can be used to immunize individuals against agents of biological warfare. The biologically active molecules include atropine, antibodies, antigens, and antibiotics. The compositions can be placed in an inhalation device for self-administration. Pulmonary delivery of TECHNOSPHERE™ encapsulated atropine, antibodies, vaccines, and antibiotics provides an accelerated onset of immunity to the targeted disease. Furthermore, the TECHNOSPHERE™ encapsulated atropine, antibodies, vaccines, and antibiotics are stable formulations, suitable for stockpiling, rapid dissemination and mass treatment.

15 Claims, 1 Drawing Sheet

COMPOSITIONS FOR TREATMENT OR PREVENTION OF BIOTERRORISM

This application claims priority to U.S. Ser. No. 60/349,628 filed Jan. 18, 2002.

BACKGROUND OF THE INVENTION

The present invention is generally in the field of methods and compositions to neutralize or treat biologicals used especially in bioterrorism or biological warfare.

Prevention of death and disease from biological warfare agents is a concern for people serving the military and for civilians. Agents used in biological warfare include nerve gases, anthrax, ricin, botulinus, cholera, tularemia, and bubonic plague.

Atropine is a nerve gas antidote. Presently, it is delivered either by injection or via the pulmonary route employing a pressurized metered dose inhaler (PMDI). Individuals who are not practiced in self-injection frequently show reluctance to self-administer a drug via injection, let alone during times of stress, such as when under attack with a chemical agent. More importantly, pulling such a device out of a pack and moving all of the clothing and other paraphernalia to reach an appropriate site for injection incurs an unacceptable delay in time of treatment.

While the PMDI does not require self-injection, it has a number of limitations. First, the PMDI can only be used effectively over a restricted temperature range (i.e. 52° F.–86° F.), and as a result is inappropriate for use in desert conditions, or in cold environments. Second, the PMDI cannot be used at high altitudes. Third, the PMDI requires the user to synchronize his breathing with the release of the pressurized aerosol to achieve an appropriate and reproducible dose. Most people have not practiced this technique and in an emergency situation would not successfully administer the necessary dose of atropine.

Anthrax disease is caused by a potent lethal exotoxin, secreted by the bacteria to its local environment. *Bacillus anthracis,* the etiologic agent of anthrax, is a large, gram-positive, nonmotile, spore-forming bacterial rod. The three virulence factors of *B. anthracis* are edema toxin, lethal toxin and a capsular antigen. *B. anthracis* is a highly lethal biological warfare agent. It is relatively easy to make, store, and use as a weapon.

If untreated, anthrax can lead to septicemia and death. Inhalational anthrax is virtually always fatal. Case-fatality rates for inhalational anthrax are thought to approach 90 to 100%. (Center for Disease Control, Atlanta, Ga.). Methods which are effective to immediately mitigate or avoid the pathogen's destruction ability (exotoxin) are essential. These may include administration of antibodies and/or antibiotic directly into the lungs, or other agents which block the action of the exotoxin. However, means to accomplish this are not currently available.

It is therefore an object of the invention is to provide compositions which can be administered before or after exposure to an agent of biological warfare to prevent death and/or infection.

A further object of the invention to provide methods for self-administration of the compositions in an emergency situation.

A further object of the invention is to provide methods for effectively immunizing individuals via the pulmonary system against agents of biological warfare.

BRIEF SUMMARY OF THE INVENTION

Compositions containing biologically active molecules encapsulated in self-assembling, diketopiperazine microspheres (TECHNOSPHEREs™) and methods for making and administering such compositions are described herein. The compositions can be used to treat or prevent infection or poisoning of individuals exposed to the biological weapons. Treatment or prevention may be by neutralization (i.e., an agent that binds to and neutralizes a nerve gas or toxin or its receptor), for example, an antibody or ligand such as atropine, by killing of the infectious agent (an antibiotic, an antiviral, antibodies), or by immunize individuals against agents of biological warfare (antigens, adjuvants, immunostimulants such as cytokines). Pulmonary delivery of TECHNOSPHERE™ encapsulated antibodies, vaccines, and/or immunostimulants can also be used to provide an accelerated onset of immunity to the targeted disease.

A small, disposable inhalation device is also described. This device can be stored in a readily accessible pocket for immediate use. The device contains a single dosage of the materials to be delivered, which is administered to the pulmonary system by compression of the device, forcing the materials into the airway of the person in need thereof. Furthermore, the TECHNOSPHERE™ encapsulated atropine, antibodies, vaccines, and antibiotics are stable formulations, suitable for stockpiling, rapid dissemination and mass treatment.

DETAILED DESCRIPTION OF THE INVENTION

I. Compositions

A. Diketopiperazine

Figure 1:
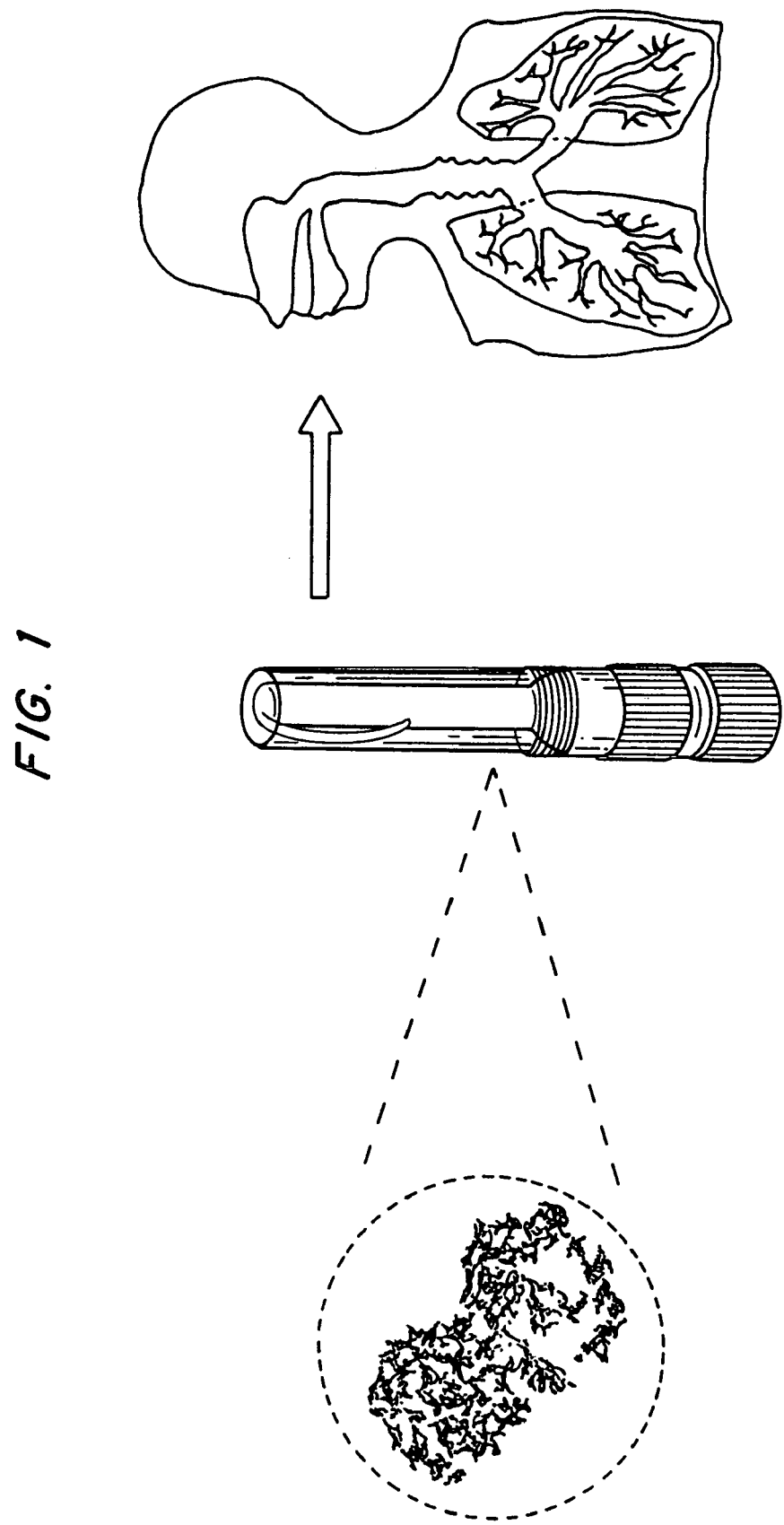
FIG. 1 is a pictorial representation of the method for delivering TECHNOSPHERE™ encapsulated bioactive molecules to the pulmonary system.

Biologically active molecules are encapsulated in self-assembling, diketopiperazine microspheres, such as TECHNOSPHEREs™. Such molecules include atropine, antibodies, antigens, and antibiotics. In some embodiments, the compositions may contain additional molecules, such as inflammatory cytokines, chemokines and lectins.

TECHNOSPHEREs™ are self-assembling, diketopiperazine microspheres, which are insoluble and stable at one pH and become unstable and/or soluble at another pH. The TECHNOSPHEREs™ are typically between 2 and less than 10 microns. In some embodiments, the TECHNOSPHEREs™ are 8 microns. In a preferred embodiment the TECHNOSPHEREs™ are 2 microns. This composition provides a perfectly sized pulmonary formulation, which ensures rapid systemic delivery of the full dose. Inhalation to the deep lung provides a rapid onset of the action.

Diketopiperazines or their analogs are soluble in bicarbonate or other basic solutions and are insoluble upon acidification by adding an acid such as citric acid. TECHNOSPHEREs™ and methods for making TECHNOSPHEREs™ are described in U.S. Pat. Nos. 5,352,461, 5,503,852, and 6,071,497, incorporated herein by reference.

$$U-Q-T-O\underset{n(H_2C)}{\overset{O}{\underset{X}{\bigcirc}}}\overset{X}{\underset{O}{\bigcirc}}(CH_2)_n$$
$$Q-T-Q-U$$

or $$U-Q\underset{n(H_2C)}{\overset{O}{\underset{X}{\bigcirc}}}\overset{X}{\underset{O}{\bigcirc}}(CH_2)_n$$
$$Q-T-Q-U$$

B. Biologically Active Agents

Treatment or prevention may be by neutralization (i.e., an agent that binds to and neutralizes a nerve gas or toxin or its receptor), for example, an antibody or ligand such as atropine, by treatment of the resulting infection (an antibiotic, an antiviral, antibodies), or by immunize individuals against agents of biological warfare (antigens, adjuvants, immunostimulants such as cytokines). Exemplary biologically active molecules include atropine, antibodies, antigens, and antibiotics.

a. TECHNOSPHERE™ Encapsulated Atropine

Atropine is encapsulated and stabilized in the TECHNOSPHEREs™. The rapid absorption of atropine provides an immediate response to nerve gas.

b. TECHNOSPHERE™ Encapsulated Antibodies

High affinity, anti-toxin, monoclonal antibodies are encapsulated in TECHNOSPHEREs™. The antibodies may bind to toxins produced by organisms such as Anthrax, ricin, botulinus, cholera, tularemia, and bubonic plague. In one embodiment, a mixture of high affinity 100% human $IgG_4$ monoclonal antibodies (mAbs) or $F(ab')_2$ fragments specific to the tripartite anthrax toxin is encapsulated in the TECHNOSPHEREs™. The $F(ab')_2$ fragments may be used to prevent rapid clearance by alveolar macrophages. The use of 100% human antibodies avoids deleterious human-antimouse immune responses, enabling multiple administrations and reducing side effects. In the preferred embodiment, the TECHNOSPHEREs™ are 2 microns.

The antibodies can be formed using standard techniques (injection of antigen into animals to prepare polyclonal antibodies, fusion of isolated antibody producing cells to produce hybridomas for production of monoclonal antibodies and/or recombinant techniques which produce heavy, light chain, or fusion antibodies) and delivered using the methods described herein.

The binding affinity of the antibodies to the virulent factors determines the degree of protection conferred through passive immunization. Passive immunization involves the administration of pre-formed antibodies into a non-immune individual. Passive immunization provides rapid action against a pathogen's toxins and can be employed as a prophylactic measure, as well as, for therapy of an acute disease, such as Anthrax.

c. TECHNOSPHERE™ Encapsulated Antigens

Antigens are administered in an effective amount to elicit a protective immune response against the antigen or the source of the antigen. The antigens can be small or large molecules, such as peptides, DNA (genomic or plasmid), mRNA, proteins, glycoproteins, mucins, glycosides or cell fractions such as extracted cell membrane, cytosol or nuclear fractions, or the organism itself, typically dead or attenuated. For the treatment of Anthrax, the vaccine contains peptides, proteins, or plasmid DNA (pX01 and pX02) encoding for Anthrax virulent factors and capsule antigens. A variety of vaccines, including those for ricin and smallpox, can be encapsulated in TECHNOSPHEREs™.

Bacterial antigens are aggregated in particles ranging from 1–100 nm and encapsulated into the TECHNOSPHEREs™. In the preferred embodiment for the treatment of Anthrax, the TECHNOSPHEREs™ are 8 microns. Larger size particles can enhance uptake by cells of the reticuloendothelial system and more rapid processing for production of antibodies or a T-cell mediated response.

Upon pulmonary administration, the TECHNOSPHEREs™ dissolve in neutral pH and the aggregated antigen is taken-up and processed by alveolar macrophages and other professional Antigen Presenting Cells (APC). The APCs migrate through the lymphatic system and disseminate in the blood stream, equipped and ready to stimulate the appropriate T cells and B cells upon physical encounter. APC refers to a variety of cells, including dendritic cells, macrophages, and B-cells. They typically have a common function of endocytosing or phagocytosing antigens, degrading them into simple molecular fragments and re-expressing fragments of the antigen on the cell surface of the APC, which the T cells recognize as antigens.

The direct targeting into professional APC by the TECHNOSPHERE™ encapsulated antigens ensures the retention of an effective local antigen dose for optimal stimulation of the immune effector cells.

To enhance immune stimulation, the TECHNOSPHEREs™ may be loaded with additional molecules, including but not limited to inflammatory cytokines, chemokines or lectins. Such molecules function as attractants and opsonins in conjunction with the antigens. Chemokines are a superfamily of small proteins, which play an important role in recruiting inflammatory cells into tissues in response to infection and inflammation. Chemokines facilitate leukocyte migration and positioning as well as other processes such as angiogenesis and leukocyte degranulation. Cytokines act as messengers to help regulate immune and inflammatory responses. The cytokine superfamily includes factors such as erythropoietin, thrombopoietin, granulocyte-colony-stimulating factor and the interleukins (or ILs).

Active immunization involves encapsulating a bacterial antigen for targeted delivery to pulmonary, professional APC. This method facilitates the priming and education of peripheral immune cells to evoke immunity against diseases, such as those spread by biological warfare.

d. TECHNOSPHERE™ Encapsulated Anti-Infectives

Antibiotics, antivirals, anti-fungals, and other compounds for use as anti-infectives can be encapsulated in the particles in an effective amount to prevent or treat infection using standard dosing techniques for pulmonary administration. A variety of FDA approved antibiotics can be encapsulated in the TECHNOSPHEREs™. Such antibiotics include synthetic peptides, Doxycycline, Penicillin G and Ciproxin. In the preferred embodiment, the antibiotics are encapsulated in TECHNOSPHEREs™ with a particle size of 2 microns.

The antibiotics are delivered directly to the pathogens in the lung, such as in the case of pulmonary anthrax. This treatment may be combined with the conventional method of antibiotic delivery, systemic administration. When antibiotics are systemically administered, they have difficulty reaching the lungs. A very high dose of antibiotic is needed to effectively treat the pathogens in the lung. Therefore, by delivering the antibiotics encapsulated in TECHNOSPHEREs™ to the lungs, a high concentration of antibiotic on the pathogen in the lung is achieved very quickly, while a lower dose of antibiotic is needed to effectively treat the lungs.

II. Methods of Making the Compositions

The biologically active molecule is encapsulated within microparticles by dissolving the diketopiperazine in solution at neutral pH, adding the biologically active molecule to be encapsulated, then solidifying the structure by adding acid, such as acetic or citric acid. Then the microparticles are washed by filtration and lyophilized to form a dry powder.

III. Methods of Administration

Referring to FIG. 1, encapsulated bioactive molecules are delivered to the pulmonary system using a device. The dotted circle contains a TECHNOSPHERE™ encapsulated bioactive molecule, which is inside the inhalation device. The person inhales the material released from the device.

The dry powdered compositions may be packaged in unit doses. Each package is placed in a delivery device, such as the device described in WO 01/07107, published Feb. 1, 2001. In one embodiment, the device may be a cylinder that is approximately 3.75 inches long and is in the shape of a cigarette. At one end of the device is a screw top. The device is activated by removing the screw top. The device is breath actuated and uses the breath as a means of propelling the powder through the device. Thus, each dose is simply inhaled as the need arises without the requirement that the individual be practiced in synchronizing his breathing. All that is required is that the individual breath in through the device as he would suck on a soda straw or draw on a cigarette. Thus, administration is more user friendly and less prone to user error than by injection or using PMDI.

The individual doses are about the size of a cigarette. Thus they are portable and can be easily distributed to military personnel or other at-risk populations. A further advantage is that one can easily monitor and track for possible abuse since the dose unit could be immediately verified as having been used or not.

The device is preferably small enough to fit inside a gas mask. Therefore if the user is wearing a gas mask, the device can be inserted under the lower part of the gas mask. Then the user can inhale the filtered air inside the gas mask.

Unlike the currently available aerosol formulations, the inhaled atropine, antigen, antibody, or antibiotic compositions are effective at high altitudes, within wide temperature ranges and at both low and high humidity.

Inhaled administration of TECHNOSPHERE™ encapsulated atropine, antibodies, vaccines, and antibiotics provides an accelerated onset of immunity to the targeted disease. Furthermore, the TECHNOSPHERE™ encapsulated active agents are stable formulations, suitable for stockpiling, rapid dissemination and mass treatment. This is due to their ease of application and the obviation of the need for medical personnel to administrate the active agents. For example, vaccines to Anthrax, smallpox and other agents of biological warfare, or anti-toxin can be administered after exposure. This technology allows military field personnel to carry a dose of the vaccination for immediate self-administration if needed.

EXAMPLES

Example 1

TECHNOSPHERE™ Encapsulated Atropine.

Atropine (Spectrum, Gardenia, Calif.) concentrations of 10 and 5 mg/mL were prepared in 1.0, 0.5 and 0.1% glacial acetic acid for use in the cryoprecipitation of Atropine/TECHNOSPHERE™. The theoretical Atropine load was 5 and 10% that was prepared from the 10 and 5 mg/mL concentrations in each of the 1.0, 0.5 and 0.1% glacial acetic acid solutions (except the 10 mg/mL in 0.1% due to poor solubility). The TECHNOSPHERE™ was suspended in 10 mL of the corresponding glacial acetic acid solution that was used to dissolve the Atropine. Then the remaining 10 or 5 mg/mL Atropine solution to yield 5% solids was added while vortexing. The 10% load using the 5 mg/mL atropine solution (there were three of these formulations) required only the atropine solution in the corresponding glacial acetic acid volume to yield the desired 5% solids. Therefore, the 10 mL that the TECHNOSPHERE™ was originally suspended in was the 5 mg/mL Atropine solution and not just the glacial acetic acid solution. The cryoprecipitated formulations were then pelleted in liquid nitrogen and dried by lyophilization.

Particle size analysis of this material showed a 69.9% of the formulation was in the size range of 0.5–5 microns. The mean particle size for the Atropine was 1.39 microns, where 90% of the particles were less than 3.0 microns and 90% of the particles were greater than 0.69 microns.

Accelerated stability studies were used to test the shelf-life for the compositions. The TECHNOSPHERE™ encapsulated atropine has a shelf-life exceeding 2 years.

Example 2

TECHNOSPHERE™ Encapsulated Vaccine for Anthrax

Vaccines containing peptides, proteins, or plasmid DNA coding for Anthrax virulent factors and capsule antigens are encapsulated in 8 micron TECHNOSPHEREs™. A soluble enhancer, Tumor necrosis factor-related activation-induced cytokine (TRANCE), is delivered subsequent to the vaccine inhalation. TRANCE binds to dendritic cells (DC), enhances the longevity and abundance of DC and promotes DC-T cell interactions.

The 8 micron size of the compositions is too large for alveolar macrophages, but ideal for DC. Therefore, these compositions directly target DC in the lung for efficient uptake of the vaccines and presentation to T-cells.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

We claim:

1. A pulmonary formulation comprising diketopiperazines having a structure selected from the group consisting of wherein n is between 0 and 7, Q is, independently, a C1–20 straight, branched or cyclic alkyl, aralkyl, alkaryl, alkenyl, alkynyl, heteroalkyl, heterocyclic, alkyl-heterocyclic, or heterocyclic-alkyl; T is —C(O)O, —OC(O), —C(O)NH, —NH, —NQ, —OQO, —O, —NHC(O), —OP(O), —P(O)O, —OP(O)2, —P(O)2O, ——OS(O)2, or —S(O)3; U is an acid group, a basic group or a zwitterionic $C_{1-20}$ chain containing at least one acidic group and at least one basic group, wherein the side chains can be further functionalized with an alkene or alkyne group at any position, one or more of the carbons on the side chain can be replaced with an oxygen, one or more of the carbons can be functionalized with an acidic or basic group, and wherein the ring atoms X at positions 1 and 4 are either O or N; or wherein the ring atoms X at positions 1 and 4 are either O or N; and at least one of the side-chain substituents R at positions 3 and 6 contains an ionizable group; and a biologically active agent selected from the group consisting of agents neutralizing toxins or nerve gases; anti-infectives, antigens, antibodies, and immunostimulants for the treatment or alleviation of symptoms of an individual exposed to a biological weapon.

2. The formulation of claim 1 wherein the biologically active agent is selected from the group consisting of drugs, receptors, receptor fragments and ligands which block the action of toxins or nerve gases, and combinations thereof.

3. The formulation of claim 2 wherein the agent is atropine.

4. The formulation of claim 1 wherein the agent is an antibiotic, antiviral or anti-fungal.

5. The formulation of claim 1 wherein the formulation comprises agents selected from the group consisting of antigens, antibodies and immunostimulatory molecules.

6. The formulation of claim 1 wherein the diketopiperazine formulation is in the form of particles packaged in a disposable device for administering the particles by inhalation to a person in need thereof.

7. A method of treating a person who has or may be exposed to a biological weapon to prevent or alleviate symptoms associated with exposure to the biological weapon comprising administering to the person a pulmonary formulation comprising diketopiperazines having a structure selected from the group consisting of wherein n is between 0 and 7, Q is, independently, a C1–20 straight, branched or cyclic alkyl, aralkyl, alkaryl, alkenyl, alkynyl, heteroalkyl, heterocyclic, alkyl-heterocyclic, or heterocyclic-alkyl; T is —C(O)O, —OC(O), —C(O)NH, —NH, —NQ, —OQO, —O, —NHC(O), —OP(O), —P(O)O, —OP(O)2, —P(O)2O, ——OS(O)2, or —S(O)3; U is an acid group, a basic group or a zwitterionic $C_{1-20}$ chain containing at least one acidic group and at least one basic group, wherein the side chains can be further functionalized with an alkene or alkyne group at any position, one or more of the carbons on the side chain can be replaced with an oxygen, one or more of the carbons can be functionalized with an acidic or basic group, and wherein the ring atoms X at positions 1 and 4 are either O or N; or

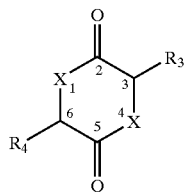

wherein the ring atoms X at positions 1 and 4 are either O or N; and at least one of the side-chain substituents R at positions 3 and 6 contains an ionizable group; and a biologically active agent selected from the group consisting of agents neutralizing toxins or nerve gases, antiinfectives, antigens, antibodies, and immunostimulants for the treatment of an individual exposed to a biological weapon.

8. The method of claim 7 wherein the biologically active agent is selected from the group consisting of rugs, receptors, receptor fragments and ligands which block the action of toxins or nerve gases, and combinations thereof.

9. The method of claim 7 wherein the agent is atropine.

10. The method of claim 7 wherein the agent is an antibiotic, antiviral or anti-fungal.

11. The method of claim 7 wherein the composition comprises agents selected from the group consisting of antigens and immunostimulatory molecules.

12. A device for use in treating or preventing an individual exposed to a biological weapon, wherein the device contains diketopiperazines particles comprising a biologically active agent selected from the group consisting of agents neutralizing toxins or nerve gases, antiinfectives, antibodies, antigens, and immunostimulants for the treatment or alleviation of symptoms of an individual exposed to a biological weapon, and the diketopiperazines have a structure selected from the group consisting of

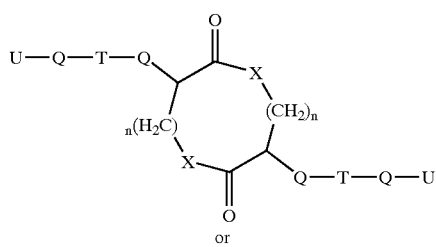

or

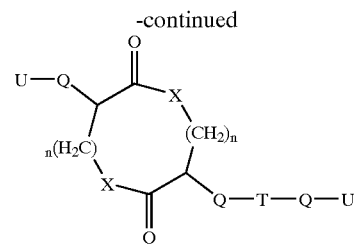

wherein n is between 0 and 7, Q is, independently, a $C_{1}$–20 straight, branched or cyclic alkyl, aralkyl, alkaryl, alkenyl, alkynyl, heteroalkyl, heterocyclic, alkyl-heterocyclic, or heterocyclic-alkyl; T is —C(O)O, —OC(O), —C(O)NH, —NH, —NQ, —OQO, —O, —NHC(O), —OP(O), —P(O)O, —OP(O)2, —P(O)2O, ——OS(O)2, or —S(O)3; U is an acid group, a basic group or a zwitterionic $C_{1-20}$ chain containing at least one acidic group and at least one basic group, wherein the side chains can be further functionalized with an alkene or alkyne group at any position, one or more of the carbons on the side chain can be replaced with an oxygen, one or more of the carbons can be functionalized with an acidic or basic group, and wherein the ring atoms X at positions 1 and 4 are either O or N; or

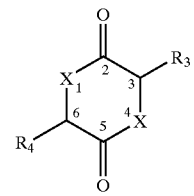

wherein the ring atoms X at positions 1 and 4 are either O or N; and at least one of the side-chain substituents R at positions 3 and 6 contains an ionizable group; and means for introducing the diketopiperazine particles into the pulmonary system of the individual.

13. The device of claim 12 wherein the device is disposable and for single use.

14. The device of claim 12 wherein the device fits with a face mask.

15. The device of claim 12 wherein the device comprises a compressible trigger to deliver the particles to the individual in need thereof.

\* \* \* \* \*

UNITED STATES PATENT AND TRADEMARK OFFICE
CERTIFICATE OF CORRECTION

PATENT NO.         : 6,991,779 B2                                      Page 1 of 1
APPLICATION NO. : 10/347932
DATED                  : January 31, 2006
INVENTOR(S)        : Solomon S. Steiner et al.

It is certified that error appears in the above-identified patent and that said Letters Patent is hereby corrected as shown below:

Column 7, lines 55-64, delete
" 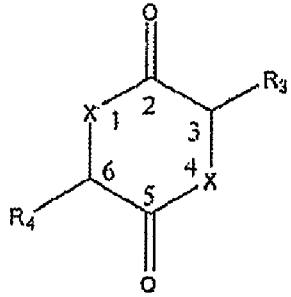 "

Column 9, line 20, replace "rugs" with --drugs--.

Signed and Sealed this

Second Day of October, 2007

JON W. DUDAS
*Director of the United States Patent and Trademark Office*